United States Patent
Nagai et al.

(10) Patent No.: US 6,855,845 B2
(45) Date of Patent: Feb. 15, 2005

(54) PROCESS FOR THE PREPARING BROMOISOPHITHALIC ACID COMPOUND

(75) Inventors: Masaki Nagai, Chiyoda-ku (JP); Hideo Suzuki, Funabashi (JP); Isao Hashiba, Funabashi (JP)

(73) Assignee: Nissan Chemical Industries, Ltd., Tokyo (JP)

(*) Notice: Subject to any disclaimer, the term of this patent is extended or adjusted under 35 U.S.C. 154(b) by 85 days.

(21) Appl. No.: 10/296,500

(22) PCT Filed: May 30, 2001

(86) PCT No.: PCT/JP01/04532

§ 371 (c)(1),
(2), (4) Date: Nov. 25, 2002

(87) PCT Pub. No.: WO01/94289

PCT Pub. Date: Dec. 13, 2001

(65) Prior Publication Data

US 2004/0015010 A1 Jan. 22, 2004

(51) Int. Cl.⁷ .......................... C07C 69/76; C07C 51/42; C07C 63/313
(52) U.S. Cl. .......................... 560/83; 562/480; 562/486; 562/487; 562/460
(58) Field of Search ................. 562/460, 480, 562/486, 487; 560/83

(56) References Cited

U.S. PATENT DOCUMENTS 2,596,945 A * 5/1952 Shokal et al. ............... 526/322
3,142,701 A * 7/1964 Graham ...................... 562/480

FOREIGN PATENT DOCUMENTS

| JP | A 54-32435 | | 3/1979 |
| JP | 10114712 | * | 3/1979 |
| JP | A 61-171452 | | 8/1986 |
| JP | A 10-114712 | | 5/1998 |

* cited by examiner

Primary Examiner—Cecilia J. Tsang
Assistant Examiner—Taylor V. Oh
(74) Attorney, Agent, or Firm—Oliff & Berridge, PLC

(57) ABSTRACT

The present invention relates to a process for preparing bromoisophthalic acid compounds, particularly 5-bromoisophthalic acid compounds and 4,5-dibromoisophthalic acid compounds comprising brominating an isophthalic acid compound of the general formula (1)

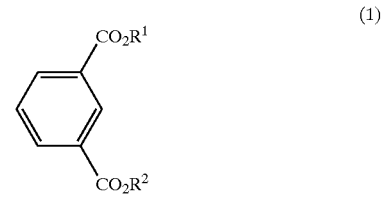

(1)

wherein $R^1$ and $R^2$ independently of one another are hydrogen atom or $C_{1-6}$ alkyl, with bromine in a solvent containing sulfur trioxide. The object of the invention is to provide a process for preparing bromoisophthalic acid compounds, particularly 5-bromoisophthalic acid compounds and 4,5-dibromoisophthalic acid compounds in a highly selective manner by using bromine that is industrially inexpensive.

4 Claims, No Drawings

PROCESS FOR THE PREPARING BROMOISOPHITHALIC ACID COMPOUND

TECHNICAL FIELD

The present invention relates to a process for preparing a bromoisophthalic acid compound comprising brominating an isophthalic acid compound of the general formula (1)

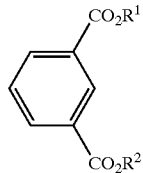
(1)

wherein $R^1$ and $R^2$ independently of one another are hydrogen atom or $C_{1-6}$ alkyl. Bromoisophthalic acid compounds are key intermediates for modifiers for several polymers represented by polyesters and polyamides, etc. or functional chemicals, and pharmaceutical preparations and agricultural chemicals.

BACKGROUND ART

Conventionally, it is known that selective bromination of aromatic compounds having an electron-attracting group is very difficult. As techniques related to such a reaction, it is known, for example as a method for preparing dialkyl 5-bromoisophtalate a method comprising brominating dimethyl isophthalate with bromine at the presence of bromine trifluoride (BrF3) to give dimethyl 5-bromoisophtalate in a 55% yield (J. Org. Chem., 58, 239 (1993)). This method, however, uses bromine trifluoride that is expensive and intractable, and leads an aimed product in a low yield. Therefore, the above-mentioned method is not practical.

An object of the present invention is to provide a process for preparing bromoisophthalic acid compounds, in particular 5-bromoisophthalic acid compounds and 4,5-dibromoisophthalic acid compounds in a selective manner and a high yield, by the use of bromine that is inexpensive industrially.

As a result that the present inventors researched eagerly on processes for preparing bromoisophthalic acid compounds and 4,5-dibromoisophthalic acid compounds can be prepared in a particularly selective manner and a high yield by the use of bromine that is inexpensive industrially, and completed the process for preparing bromoisophthalic acid compounds of the present invention.

DISCLOSURE OF INVENTION

That is, the present invention relates to a process for preparing a bromoisophthalic acid compound comprising brominating an isophthalic acid compound of the general formula (1)

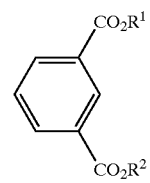
(1)

wherein $R^1$ and $R^2$ independently of one another are hydrogen atom or $C_{1-6}$ alkyl, with bromine in a solvent containing sulfur trioxide.

It is very difficult to brominate compounds having an electron-attracting group on its aromatic ring, such as isophthalic acid. Therefore, in the prior art, even if the reaction proceeds, it gives the corresponding compounds only in a low yield. The present inventors found reaction conditions, such as the amount of sulfur trioxide, reaction temperature and reaction time by which monobromo and dibromo products can be prepared in a high yield and a selective manner.

Hereinafter, the present invention will be described in detail.

Isophthalic acid compounds as a raw material are compounds of the general formula (1)

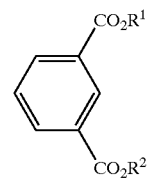
(1)

wherein $R^1$ and $R^2$ independently of one another are hydrogen atom or $C_{1-6}$ alkyl. $R^1$ and $R^2$ include specifically hydrogen, methyl, ethyl, n-propyl, i-propyl, n-butyl, i-butyl, s-butyl, t-butyl, 1-pentyl, 2-pentyl, 3-pentyl, 3-methylbutyl, neopentyl, t-pentyl, 1-hexyl, 2-hexyl, 3-hexyl, 1-methyl-1-ethylpropyl, 1,1,2-trimethyl propyl, 1,2,2-trimethyl propyl, 3,3-dimethyl butyl and the like.

Further, the isophthalic acid compounds of the general formula (1) include isophthalic acid, or dialkyl isophthalate compounds, such as dimethyl isophthalate, diethyl isophthalate, methyl ethyl isophthalate, di-n-propyl isophthalate, di-i-propyl isophthalate, di-n-butyl isophthalate, di-1-pentyl isophthalate, di-1-hexyl isophthalate, di-1-pentyl isophthalate and di-1-hexyl isophthalate. Among them, isophthalic acid and dimethyl isophthalates are preferable from the standpoint of availability of industrial raw materials. Particularly, isophthalic acid is appropriate for a raw material in the present reaction because it can be produced economically and its commercial product can be used at it is.

A characteristic of the present invention resides in bromination with bromine in a solvent containing sulfur trioxide. Conventionally, it is known that compounds in which hydrogen atoms on the phenyl group are substituted with electron-attracting groups, such as isophthalic acid hardly reacts by the use of only bromine. The present inventors attempted to an reaction with the bromine improved in its brominating ability by forming a complex between sulfur trioxide and bromine. Consequently, they found that monobromo products can be obtained, and further dibromo products also can be obtained by setting suitable conditions.

As the solvent containing sulfur trioxide, organic solvents can be used, but it is generally convenient to use sulfuric acid solvent, that is fuming sulfuric acid. Also, it is able to use chlorosulfonic acid, sulfur trioxide-dioxane complex, sulfur trioxide-pyridine complex or the like that is a complex between sulfur trioxide and other compound. Among them, fuming sulfuric acid affords high reactivity in a reduced cost.

In a case where monobromo products are prepared, it is enough to use sulfur trioxide in an amount of number of moles no more than that of bromine in order to obtain a high selectivity.

On the other hand, in a case where dibromo products are prepared, it is favorable to use sulfur trioxide in an amount of number of moles no less than that of bromine.

On the form of fuming sulfuric acid, the concentration of sulfur trioxide may be broadly selected, but commercially available products having a concentration of 10 to 60 wt % can be generally used. Also, fuming sulfuric acid having a concentration no more than 10 wt % can be prepared by adding sulfuric acid to the commercially available products.

Although the reaction is influenced by other conditions therefor, lower concentration (1 to 30 wt %) of sulfur trioxide in fuming sulfuric acid is appropriate for preparing monobromo products, and higher concentration thereof (10 to 60 wt %) is appropriate for preparing dibromo products.

As a solvent, hydrocarbon halides or sulfolane can be used besides the above-mentioned sulfuric acid.

Concrete example of hydrocarbon halides include carbon tetrachloride, 1,2-dichloroethane (EDC), 1,1,1-trichloroethane, 1,1,2-trichloroethane and 1,1,2,2-tetrachloroethane. It is preferably appropriate to use it in an amount in weight of 1 to 20 times, particularly 2 to 10 times that of substrate.

The brominating reaction of the present invention is characterized by using bromine that is the most economic in industrial use. Commercially available bromine can be used as it is. The amount of bromine used is preferably 0.5 to 1.5 time in moles that of substrate in a case where monobromo products are prepared, and preferably 1 to 3 times in moles that of substrate in a case where dibromo products are prepared. In the meantime, the proportion of monobromo and dibromo products formed can be selected by sulfur trioxide concentration, reaction temperature and reaction time besides amount of bromine used.

It is necessary for the present reaction to be carried out with heating, and the reaction is carried out generally under pressure. The reaction can be carried out at a temperature of 50° to 200° C., particularly 100° to 160°. The reaction time ranges generally from 1 to 100 hours although it changes depending on the kind of substrate, the amount of fuming sulfuric acid, the amount of bromine or the reaction temperature, and the reaction ceases generally for 3 to 24 hours. In addition, the end point of the reaction can be confirmed by gas chromatography or liquid chromatography. The present reaction may be carried out in a batch system or a continuous system.

After the reaction is completed, a reaction solution is added into a large excess of cooled water, and crystals separated out are filtered off, washed with water and dried to give crude crystals of aimed bromo products. In addition, the crude crystals can be optionally purified by recrystallization.

The present inventors examined several solvents for recrystallization, and consequently found that it is impossible for bromoisophthalic acid to be recrystallized with general solvents for recrystallization due to its slight solubility. On the contrary, the present inventors found that lower alcohol solvents with 1 to 5 carbon atoms give aimed products in high yield of recrystallization and high purity. Among them, particularly methanol is preferable as the solvent as it exhibits good ability for recrystallization and advantage economically.

The present inventors found that a distillation method is applicable as another method for purifying the bromo products produced by the present invention. That is, crude crystals of bromoisophthalic acid obtained by the reaction are diesterified with a lower alcohol solvent with 1 to 5 carbon atoms in the presence of an acid catalyst, and then the aimed bromo products can be separated from esters of unreacted raw materials and other dibromo products by the use of distillation. As the acid catalyst, sulfuric acid or p-toluene sulfonic acid can be used. It is preferable to use the acid catalyst in an amount of 1 to 20 mol % based on that of isophthalic acid compounds. On the other hand, among lower alcohol solvents with 1 to 5 carbon atoms, methanol or ethanol is preferable from the standpoint of boiling point of the diesters. The amount used thereof is generally 5 to 100 times in moles that of isophthalic acid compounds.

The reaction can be generally carried out at a boiling point of an alcohol used, but ceases for a short time by carrying out it at a temperature above the boiling point of the alcohol under pressure. In a case where methanol is used, the temperature is preferably 100° to 180° C.

It is preferable to carry out the reaction under reduced pressure as each of the resulting esters has a high boiling point. Generally, it is preferably carried out at 10 to 10000 Pa. Although simple distillation can be carried out depending on the component of the reacted products, generally the aimed monobromo products with a high purity are obtained by rectification.

Although dibromo products can be distilled out as faints after a distillation, they can be isolated by recrystallization of a still residue after monobromo products were distilled out.

In the meantime, when monobromo products are produced selectively, there is a fear that dibromo products might be produced as the present reaction is a successive reaction. Therefore, it is preferable to recycle raw materials by interrupting the reaction and making only isophthalic acid compounds and monobromo isophthalic acid compounds present in the reaction system. And, as mentioned above, an esterification with lower alcohol solvents with 1 to 5 carbon atoms is carried out and then a distillation is carried out.

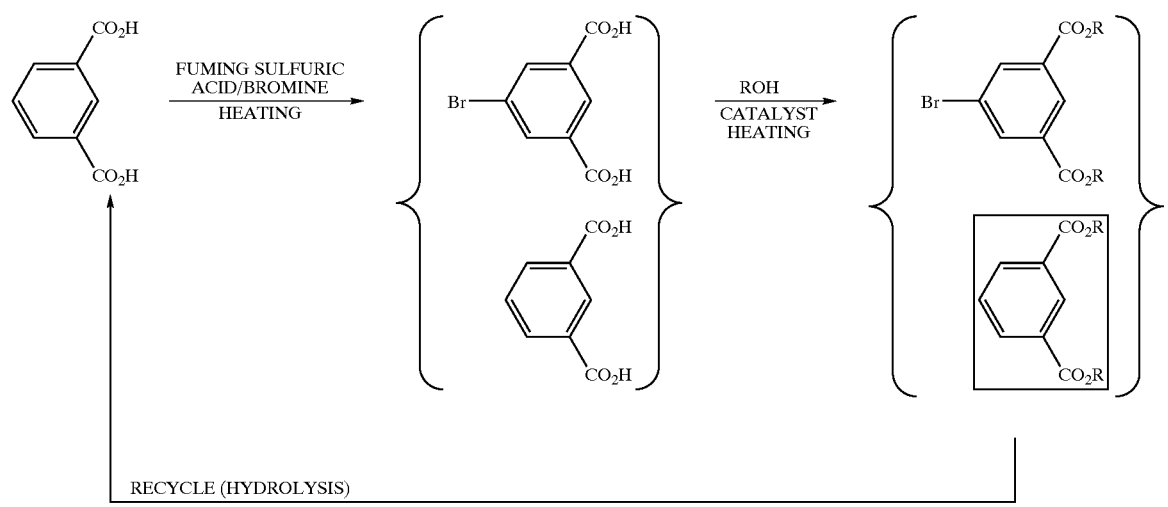

(R is lower alkyl with 1 to 5 carbon atoms.)

BEST MODE FOR CARRYING OUT THE INVENTION

Hereinafter, the present invention is described more concretely on the basis of examples to which the present invention is not limited.

EXAMPLE 1

Into a 50 ml pressure and sealable glass tube, 1.66 g (10 mmol) of isophthalic acid, 6.00 g of 10 wt % fuming sulfuric acid and 1.6 g (10 mmol) of bromine were charged, and the content was stirred at 130° C. for 22 hours. After the conclusion of the reaction, the content was cooled to room temperature, and placed in a beaker containing ice water to give a solid. The resulting solid was filtered off, washed with cooling, and further dried under reduced pressure to give 2.41 g (purity: 83.5%) of a crude crystal of the aimed product (yield: 81.9%). Then, the crystals were solved in 10 g of methanol at 60° C., cooled to room temperature, and thereafter filtered off to give 1.61 g (purity: 100%) of a white crystal (yield of recrystallization: 80.1%). This crystal was identified as 5-bromoisophthalic acid by MASS, $^1$H-NMR and melting point.

EXAMPLES 2 to 7

Procedures were carried out similarly to that of Example 1 except that the reaction temperature, the concentration of fuming sulfuric acid and the amount of bromine were changed. The results on the resulting monobromo products were shown in Table 1.

TABLE 1

| Ex. No. | Concentration of Fuming Sulfuric Acid (wt %)-(g) | Bromine g(mmol) | Temperature(° C.) | Time (h.) | Quantitative Yield (%) | | | |
|---|---|---|---|---|---|---|---|---|
| | | | | | 5BIP | IP | 4,5-DBIP | 2,5-DBIP |
| 2 | 10-6 | 1.6(10) | 110 | 22 | 34.5 | 58.0 | trace | — |
| 3 | 20-6 | 1.6(10) | 110 | 22 | 48.6 | 43.2 | trace | — |
| 4 | 30-6 | 1.6(10) | 110 | 22 | 62.8 | 24.6 | 2.3 | — |
| 5 | 10-6 | 1.6(10) | 150 | 22 | 77.0 | 4.1 | 8.0 | — |
| 6 | 20-6 | 1.6(10) | 150 | 7 | 53.8 | 46.5 | 0.7 | — |
| 7 | 10-6 | 3.2(20) | 150 | 7 | 79.1 | 6.4 | 5.8 | trace |

IP: Isophthalic Acid, 5BIP: 5-Bromoisophthalic Acid,
4,5-DBIP: 4,5-Dibromoisophthalic Acid
2,5-DBIP: 2,5-Dibromoisophthalic Acid

EXAMPLE 8

Into a 50 ml pressure and sealable glass tube, 1.66 g (10 mmol) of isopthalic acid, 6.00 g of 30 wt % fuming sulfuric acid and 1.6 g (10 mmol) of bromine were charged, and the content was stirred at 150° C. for 22 hours. After the conclusion of the reaction, the content was cooled to room temperature, and placed in a beaker containing ice water to give a solid. Then, the resulting solid was filtered off, washed with cooling, and further purified by column chromatography on silica gel (chloroform/methanol=6/1, v/v) to give 0.51 g (yield: 20.7%) of 5-bromoisophthalic acid, 0.76 g (yield: 23.5%) of 4,5-dibromoisophthalic acid and 0.07 g (yield: 2.1%) of 2,5-dibromoisophthalic acid. These crystals were identified by MASS, $^1$H-NMR and melting point.

EXAMPLES 9 to 16

Procedures were carried out similarly to that of Example 8 except that the reaction temperature, the concentration of fuming sulfuric acid and the amount of bromine were changed. The results on the resulting monobromo and dibromo products were shown in Table 2.

sulfuric acid and 10.40 g (100 mmol) of bromine were charged, and the content was stirred at 120° C. for 7 hours. After the conclusion of the reaction, the content was cooled to room temperature, and placed in a beaker containing ice water to give a solid. The resulting solid was filtered off, washed with cooling, and further dried under reduced pressure to give 11.95 g of a crude crystal of the aimed product (reaction yield: 50.4% 5-bromoisophthalic acid, 19.6% isophthalic acid, 4.9% 2,5-dibromoisophthalic acid, 7.2% 4,5-dibromoisophthalic acid, 7.0% dimethyl 5-bromoisophthalate, 1.5% dimethyl isophthalate, 0.9% dimethyl 2,5-dibromoisophthalate and 0.2% dimethyl 4,5-dibromoisophthalate). Then, dimethyl esters were derived from the crystal by heating and stirring it with 65.50 g (2.04 mol) of methanol and 1.75 g (30 mol %) of sulfuric acid in an autoclave at 120° C.

In succession, the esters were subjected to rectification to give 6.73 g (yield: 49.3%, vacuum boiling point: 159° C./4.8mmHg) of aimed dimethyl 5-bromoisophthalate and 1.67 g (yield: 17.2%, vacuum boiling point: 133° C./4.8mmHg) of dimethyl isophthalate corresponding to a raw material. The resulting crystals were identified as dim-

TABLE 2

| Ex. No. | Concentration of Fuming Sulfuric Acid (wt %)-(g) | Bromine g(mmol) | Temperature(° C.) | Time (h.) | Quantitative Yield (%) | | | |
|---|---|---|---|---|---|---|---|---|
| | | | | | 5BIP | IP | 4,5-DBIP | 2,5-DBIP |
| 9  | 60-6  | 1.6(10) | 110 | 22 | 45.0 | 1.4 | 18.7 | 1.0 |
| 10 | 20-6  | 1.6(10) | 130 | 22 | 49.2 | 0.0 | 15.3 | trace |
| 11 | 30-6  | 1.6(10) | 130 | 22 | 53.1 | 0.8 | 13.6 | 1.0 |
| 12 | 20-6  | 1.6(10) | 150 | 22 | 43.1 | 0.0 | 20.0 | 0.8 |
| 13 | 20-6  | 3.2(20) | 150 | 7  | 37.5 | 0.0 | 23.3 | 1.5 |
| 14 | 10-12 | 1.6(10) | 150 | 7  | 47.0 | 0.6 | 18.1 | 1.2 |
| 15 | 20-12 | 1.6(10) | 150 | 7  | 49.8 | 0.7 | 20.3 | 1.4 |
| 16 | 20-12 | 3.2(10) | 150 | 7  | 11.9 | 0.0 | 26.2 | 4.9 |

IP: Isophthalic Acid, 5BIP:5-Bromoisophthalic Acid,
4,5-DBIP: 4,5-Dibromoisophthalic Acid
2,5-DBIP: 2,5-Dibromoisophthalic Acid

EXAMPLE 17

Into a 50 ml pressure and sealable glass tube, 1.66 g (10 mmol) of isopthalic acid, 6.00 g of 10 wt % fuming sulfuric acid and 1.6 g (10 mmol) of bromine were charged, and the content was stirred at 150° C. for 7 hours. After the conclusion of the reaction, the content was cooled to room temperature, and placed in a beaker containing ice water to give a solid. The resulting solid was filtered off, washed with cooling, and further dried under reduced pressure to give a crude crystal of the aimed product. Then, dimethyl esters were derived from the crystal by heating and stirring it at 120° C. with 13.1 g (408 mmol) of methanol and 0.35 g (30 mol %) of sulfuric acid in an autoclave. In succession, the esters were subjected to rectification to give 1.78 g (yeild: 65.1%, vacuum boiling point: 159° C./4.8 mmHg) of aimed dimethyl 5-bromoisophthalate and 0.52 g (yield: 26.8%, vacuum boiling point: 133° C./4.8mmHg) of dimethyl isophthalate corresponding to a raw material. The resulting crystals were identified as dimethyl 5-bromoisophthalate and 5-bromoisophthalic acid by MASS, $^1$H-NMR and melting point.

EXAMPLE 18

Into a 100 ml pressure and sealable glass tube, 9.70 g (50 mmol) of dimethyl isophthalate, 30.00 g of 10 wt % fuming ethyl 5-bromoisophthalate and 5-bromoisophthalic acid by MASS, $^1$H-NMR and melting point.

Industrial Applicability

According to the process of the present invention, 5-bromoisophthalic acid compounds can be prepared in a selective manner and a reduced cost.

What is claimed is:

1. A process for preparing 5-bromoisophthalic acid compound comprising brominating an isophthalic acid compound of the general formula (1)

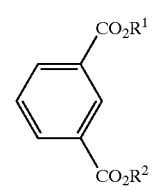

(1)

wherein $R^1$ and $R^2$ independently of one another are hydrogen atom or $C_{1-6}$ alkyl, with bromine in fuming sulfuric acid containing sulfur trioxide in a concentration of 1 to 30 wt % at a reaction temperature between 100° and 160° C.

2. A process for preparing 5-bromoisophthalic acid diester compound comprising the steps of:

brominating an isophthalic acid compound of the general formula (1)

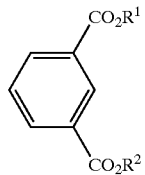

(1)

wherein $R^1$ and $R^2$ independently of one another are hydrogen atom or $C_{1-6}$ alkyl, with bromine in a molar amount 0.5 to 1.5 times that of the isophthalic acid compound in fuming sulfuric acid containing sulfur trioxide in a concentration of 1 to 30 wt % at a reaction temperature between 100° C. and 160° C. to produce a crude product;

diesterifying the resulting crude product with a lower alcohol with 1 to 5 carbon atoms at the presence of an acid catalyst to a diesterified compound; and then separating and purifying the diesterified compound by distillation.

3. The process for preparing 5-bromoisophthalic acid diester compound according to claim 2, wherein the acid catalyst is sulfuric acid, and the diesterification is carried out under pressure at a reaction temperature above the boiling point of the lower alcohol with 1 to 5 carbon atoms.

4. The process for preparing 5-bromoisophthalic acid diester compound according to claim 2, wherein the lower alcohol with 1 to 5 carbon atoms is methanol or ethanol.

* * * * *

UNITED STATES PATENT AND TRADEMARK OFFICE
CERTIFICATE OF CORRECTION

PATENT NO. : 6,855,845 B2  Page 1 of 1
APPLICATION NO. : 10/296500
DATED : February 15, 2005
INVENTOR(S) : Masaki Nagai et al.

It is certified that error appears in the above-identified patent and that said Letters Patent is hereby corrected as shown below:

On the title page item (54) and col. 1, line 2,
In the TITLE, replace "BROMOISOPHITHALIC" with --BROMOISOPHTHALIC--.

On the title page before "(51) Int. Cl. $^7$ ............ C07C 69/76; C07C 51/42;"
insert --(30)      Foreign Application Priority Data
      Jun. 5, 2000      (JP) ………………...…………...JP 2000-167511--.

Signed and Sealed this

Tenth Day of October, 2006

JON W. DUDAS
*Director of the United States Patent and Trademark Office*